(12) United States Patent
Rubin

(10) Patent No.: US 11,590,186 B2
(45) Date of Patent: *Feb. 28, 2023

(54) INDIGENOUS CBD ORAL DOSAGE FORMS

(71) Applicant: Fermented Farmer, LLC, Summertown, TN (US)

(72) Inventor: Jordan Seth Rubin, College Grove, TN (US)

(73) Assignee: Fermented Farmer, LLC, Summertown, TN (US)

( * ) Notice: Subject to any disclaimer, the term of this patent is extended or adjusted under 35 U.S.C. 154(b) by 163 days.

This patent is subject to a terminal disclaimer.

(21) Appl. No.: 16/781,489

(22) Filed: Feb. 4, 2020

(65) Prior Publication Data

US 2021/0106532 A1    Apr. 15, 2021

Related U.S. Application Data

(60) Provisional application No. 62/912,930, filed on Oct. 9, 2019.

(51) Int. Cl.

| | | |
|---|---|---|
| *A61K 31/352* | (2006.01) | |
| *A61K 36/06* | (2006.01) | |
| *A61K 31/05* | (2006.01) | |
| *A61K 9/20* | (2006.01) | |
| *A61K 9/48* | (2006.01) | |
| *A61K 36/185* | (2006.01) | |
| *A61K 9/14* | (2006.01) | |

(52) U.S. Cl.
CPC ............... *A61K 36/06* (2013.01); *A61K 9/14* (2013.01); *A61K 9/20* (2013.01); *A61K 9/48* (2013.01); *A61K 31/05* (2013.01); *A61K 31/352* (2013.01); *A61K 36/185* (2013.01); *A61K 2236/17* (2013.01); *A61K 2236/19* (2013.01)

(58) Field of Classification Search
CPC ............................... A61K 31/352; A61K 8/97
See application file for complete search history.

(56) References Cited

U.S. PATENT DOCUMENTS

| | | | | |
|---|---|---|---|---|
| 2016/0081381 A1* | 3/2016 | Medoff | ................. | A61Q 19/00 514/777 |
| 2019/0015383 A1* | 1/2019 | Woelfel | ................. | A61K 31/05 |

* cited by examiner

*Primary Examiner* — Benjamin J Packard
(74) *Attorney, Agent, or Firm* — Barbara E. Johnson

(57) ABSTRACT

The present invention is a cannabidiol oral dosage form including predominantly or exclusively hemp pomace, compounded as a tablet or formulated within a capsule without the addition of synthetic excipients, fillers or other additives, not including the inevitable presence of some moisture and the optional presence of fungal or bacterial probiotics introduced prior to or during dosage form manufacturing, and with or without fermentation of the hemp pomace prior to the dosage form manufacturing process. The dosage forms contain dietary fiber, important to activity as the desired delivery system, having a ratio of one part soluble dietary fiber to 30 parts insoluble dietary fiber and delivers desirable/non hallucinogenic cannabinoids (CBD, CBG) in a ratio of 30:1 up to 120:1 to hallucinogenic cannabinoids (THC).

5 Claims, No Drawings

INDIGENOUS CBD ORAL DOSAGE FORMS

CROSS-REFERENCE TO RELATED APPLICATIONS

This patent application claims priority to, and incorporates herein by reference, U.S. Provisional Patent Application 62/912,930 filed 9 Oct. 2019.

FIELD OF THE INVENTION

The invention pertains to improved CBD (and related cannabinoid) delivery methods and dosage forms.

BACKGROUND OF THE INVENTION

*Cannabis* indica, *Cannabis sativa* and *Cannabis ruderalis* have had a long (and truly only recently putatively dishonorable) history, indisputably from very early human horticulture. As of this writing, The History Channel recently devoted an entire special issue magazine to the story of *Cannabis* throughout the world, indicating (without limitation) that Queen Victoria's physician probably prescribed versions of *Cannabis* medicaments for pain management, and so forth. With a historic fast forward to the 2018 "Farm Bill" (Agricultural Improvements Act of 2018, 115th Congress, 2017-2018) the United States law now acknowledges that industrial hemp, a *Cannabis* plant with less than 0.3% tetra hydro cannabinol (THC) is not "marijuana" for the purpose of the Controlled Substances Act. This means that hemp-derived cannabidiol (CBD) and related cannabinoids such as cannabigerol (CBG) and cannabichromene (CBC) can now ostensibly be produced and sold as a consumable agricultural products in the United States, whereas prior to the 2018 Farm Bill hemp could be grown and used in the U.S. only for research purposes under individual states' pilot programs and in certain categories such as clothing, industrial materials and products made from the plant's stalks or seeds. In other words, 2018 was a watershed year for health care providers, consumer packaged goods companies and the pharmaceutical industry, creating for the first time a legal (or nascently legal) domestic source of cannabinoids (primarily CBD)—from U.S.grown hemp.

This watershed has led to a predictable avalanche of hemp growing, extraction, formulation and processing in the United States, to produce CBD and a myriad of products containing it. As a result, more-retail-cash-registers-than-not offer various CBD products for sale—sometimes many edible offerings such as individually wrapped chocolates containing CBD along with CBD topicals, oils and capsules—and of course online sales are brisk as well. CBD has long been known for its pain relieving, relaxing, sleep supporting, anxiety reducing benefits, rather than intoxicant properties, and sales of CBD containing products have been understandably swift and growing in the U.S. from 2018 to date.

As with any newly popular ingredient, there are opportunities for high quality products as well as those of lesser value and benefit. There are currently reliable, responsible cannabinoid rich hemp growers, manufacturers and, presumably, also formulators and peddlers reminiscent of the "snake oil salesmen" of the American 1800s. This "snake oil" analogy is apt, because Chinese snake oil was a legitimate anti-inflammatory substance for decades if not centuries, prior to faux iterations that appeared later in the U.S. The original Chinese snake oil was made from the oil of the Chinese water snake, which was rich in the omega-3-fatty acids that are known to reduce inflammation. This "snake oil" in its original form was indeed effective as a topical medicament to treat arthritis and bursitis and, eventually, the story and erstwhile product made its way to the United States—if not the omega-3-rich water snake itself, or its curative extract. The point here is that with CBD, as with anything else, responsible sourcing, processing and quality control in manufacturing are the bedrock of any superior pharmaceutically active agent. The pressures of manufacturing in light of a population clamoring for CBD are particularly intense, in world in which side-effect- or addiction-minimized pain management is still an elusive if (not scandal-laden) goal.

It is interesting that, as a general practice regarding naturally-occurring active agents—and particularly those of herbal sources—there seems to be a knee-jerk compulsion to extract the active agent compound from its botanical herb or spice. This is epitomized by extracting and synthesizing *digitalis* from foxglove, a natural herb, marketed as a pharmaceutical. In theory there is nothing wrong with extraction processes—although in practice there can indeed be negative implications to extraction, in particular as to the molecule(s) to be extracted. Extraction agents such as petroleum or coal-tar derived solvents can create residues or even alter the chemical composition of the sought-after molecule. Worse, beneficial co-factors present in the natural product in this case an herb can be separated from the active agent so as to lose the synergy of administration of the whole herb with it's known and yet-to-be discovered compounds. Even today, when *Cannabis* indica, *Cannabis sativa* and *Cannabis ruderalis* are on the brink of becoming "health food" [so to speak] instead of "Just Say No!" fodder, the temptation seems to be ubiquitous to extract and isolate key constituents within them, in order to obtain their active agent(s) for further commercialization. The question which the present inventor asked, though, was—whether traditional extraction or isolation is the only processing method that can deliver the true benefits of hemp?

SUMMARY OF THE INVENTION

The present medicament and pharmaceutical, nutraceutical and treatment method and method for delivering an active agent, centeres on a powdered form of extracted hemp pomace containing cannabinoids including CBD, dietary fiber of a particular ratio, vitamins, minerals, flavonoids, terpenes, fatty acids and amino acids, which powder is blended with other botanical ingredients or compressed into a tablet form for administration to or consumption by an animal or human in need of a reliably sourced CBD (or other cannabinoid) oral dosage form. Optionally, such dosage forms may also include natural organisms (bacteria, yeast, complex fungi, etc.), which may be present and/or allowed to proliferate or ferment, and inevitably a certain degree of moisture (water). While the present extracted hemp pomace is well suited to use alone, it may be admixed with other ingredients, whether active agents or excipients, fillers or comestible ingredients comprising dietary supplements or functional food ingredients. "Spent extracted hemp biomass" is a co-product of cannabinoid (CBD, CBG etc) extraction—preferably an organic process without the use of toxic solvents or their derivatives. As with all extraction methods and the limited yields one can expect from an extraction process, in fact there is a sizeable fraction of cannabinoids (CBD) remaining in hemp pomace. Even more importantly, however, the CBD/cannabinoid(s) in the hemp pomace contain naturally occurring co-factors, known and currently unknown, including without limitation other cannabinoids, dietary fiber, fatty acids, amino acids, terpenes and flavonoids, which enhance any or all of delivery, bioavailability and efficacy of the CBD/cannabinoid(s) in vivo. As simple as it sounds in hindsight, a key part of the present invention inheres in the ability to use predominantly or completely a hemp pomace constituent as the tablet or capsule (or equivalent) ingredient in a CBD/cannabinoid oral dosage form, typically after having been carefully dried and potentially activated through de-carboxylation of cannabinoids. Another key component to the invention is in the engineering of the delivery system, with a beneficial soluble dietary fiber (SDF)/insoluble dietary fiber (IDF) ratio of 1:30 SDF/IDF allowing for effective formulation and delivery of key constituents. The process of creating hemp pomace using natural, non toxic forms of extraction, tends to increase the ratio (increasing the percentage) of non hallucinogenic/addictive cannabinoids such as CBD, CBG, CBC to hallucinogenic/addictive cannabinoids, i.e. THC. For example, many native hemp species have a ratio of CBD: THC of 20:1, whereas the process of producing pomace in accordance with this invention results in a CBD:THC ratio of between 30:1 to as high as 100:1. In addition, hemp pomace is uniquely suitable for tabletting without additional additives, diluents or synthetic excipients—or the hemp pomace may be included in standard "hard shell" capsule, mixable powder or other dosage forms known to those skilled in the art.

DETAILED DESCRIPTION OF THE INVENTION

As with popular or over-the-counter dosage forms, particularly for active agents known to control pain, dosing is tantamount to safe and effective treatment. When it comes to CBD, general dosing guidelines suggest that a good starting dose is somewhere in the range of 1-5 mg once or twice a day, for an averaged sized human patient, with possible ethical dosing of up to 20 mg or more taken as often as three times per day. Veterinary dosing is generally pro rata by body mass/weight. As the CBD industry matures, inevitably further dosing guidelines will become available—but as with all active agents a serious challenge is to prevent inadvertent (or intentional) overdose. One benefit of the present formulations inheres in the lower cannabinoid (i.e. CBD) concentration of hemp pomace along with synergistic co-factors which provides a more balanced, "whole food" effect with less chance of deleterious side effects. A simultaneous benefit of the hemp pomace is that, whereas the CBD (or other cannabinoid) content has been reduced compared to the native hemp, the ratio of soluble dietary fiber (IDF) to insoluble dietary fiber remains the same as in the native hemp. This SDF/IDF ratio is 1:30, that is, for every 1 part of soluble dietary fiber in the hemp pomace, there is also 30 parts insoluble dietary fiber. This SDF/IDF ratio is discussed further, below.

Even though the hemp pomace of the invention is the co-product of cannabinoid (CBD) extraction, this does not mean that it does not still contain meaningful amounts of cannabinoids, such as CBD. In the analogous case of wine making, after pressing of the fermented grapes, a large portion of the beneficial, natural compounds—such as resveratrol—remain in the grape pomace as has been detailed in published research and prior art. The importance of this analogy is that even hemp pomace resulting from a natural extraction process can be relatively rich in cannabinoids such as CBD, that is, contains on the order of 10-25% or so of the original CBD content of the pre-extraction "native" hemp biomass. All of this can be simply controlled by process monitoring and testing well known in the art.

The importance of the previous paragraph has to do with unit dosage form preparation of hemp pomace. If hemp has, for example, a starting content of 10% CBD, removal of 75-90% of that amount of CBD will yield (say) a 1-2.5% CBD content in the hemp pomace. This means that for every gram of hemp pomace, the intrinsic remaining CBD in the hemp pomace is on the order of 10-25 mg, which is right in the range of a standard unit dosage form and dosing amount. These levels are theoretical and can be monitored and adjusted in real life manufacturing settings. For illustrative purposes, then, if a gram of hemp pomace contains 15 mg of CBD, it is readily possible to formulate 1 mg, 3 gm, 5 mg, 10 mg and even 20 mg CBD dosage forms by selecting the appropriate fraction of a gram of hemp pomace, or possibly slightly more than one gram, per unit dosage form. Larger serving sizes of tablets or capsules can thus contain up to 20 mg CBD while still having a size that can be consumed without difficulty. The ability of hemp pomace (with or without bacterial or fungal fermentation) to be formulated into oral dosage form capsules—or to be tabletted directly without additives—means that creation of dosing per unit is straightforward and well within the skill of the art. In fact, one of the surprisingly beneficial aspects of the present invention is the ability of hemp pomace to be tabletted or otherwise crafted into unit dosage forms without needing additives, or synthetic excipients, fillers or binders.

Any fungal or bacterial organism may be introduced to the hemp pomace before or during dosage form preparation. The optional probiotic inclusion is the main exception, besides moisture, to the inventive premise that, overall, the dosage form material (apart from a capsule if necessary) is predominantly or completely hemp pomace. Fungal and bacterial organisms are well known in the art and need not be listed here. If the hemp pomace is fermented prior to dosage form creation, such is within the scope of the invention—or probiotics may be co-formulated with the hemp pomace without prior or concurrent fermentation also.

It almost goes without saying that organically sourced hemp, extracted without hydrocarbon-based or petroleum or coal tar derived solvents, is the best choice for hemp pomace according to the present invention. By using organic hemp and avoiding noxious extraction solvents, the presence of pesticides or other solvent residues or undesirable adulterants in the hemp pomace is reduced to a beneficial minimum. Not only is the reduction of these extraneous contaminants good in and of itself, but the absence of unwanted residues maximizes the original confluence of the indigenous cannabinoids such as CBD with its synergistic co-factors, known (see list above) or unknown.

Hemp pomace according to the present invention is typically dried, possibly "activated" through de-carboxylation and co-minuted prior to tabletting or encapsulating. Dehydration to a moisture content of below 15%, preferably below 10% and more preferably to 5-6% is important in the creation of the present oral dosage forms. The co-minution may be but need not be to a (small) particle size generally within the range of powders. Generally speaking, hemp pomace particles of at least 100 microns in diameter, up to irregularly shaped particles of up to about 5 mm in their longest dimension, are best for tableting or encapsulating according to the present invention. Surprisingly, hemp pomace particles of this size are beneficially self tabletting without added ingredients and with a minimum of compression energy, that is, not enough pressure to generate significant heat. Avoidance of excessive processing also prevents the generation of unwanted heat that can denature cannabinoids (CBD), terpenes or additional cofactors in the hemp pomace. Having said that, however, the administration of hemp pomace as a powder (that is, in traditional powder particle size distributions smaller than 100 microns) and as predominantly the only oral dosage form constituent as described above—is still within the scope of the present invention.

The primary disclosure of this patent application is directed to dosage forms in which—with few exceptions such as added inert excipients, probiotics, botanicals, vitamins and minerals or adjusted or retained moisture—hemp pomace is the main ingredient in an oral dosage form. Having said that, there is a specialized application for hemp pomace, with or without probiotic, as a non-predominant dosage form additive, that is, as an excipient, usually as a hardening agent. The properties of hemp pomace are so advantageous for oral dosage form preparation that, even apart from the main embodiment of the invention in which hemp pomace is administered predominantly by itself, hemp pomace is also uniquely useful as a hardening agent and excipient for other oral dosage forms. The hemp pomace used as a hardening agent or pharmaceutical excipient may be employed with or without fermented, or co-formulated, probiotic, such as bacteria or fungus. By the same token, the emphasis in the present disclosure is on hemp pomace, for all the benefits above described, and yet it is equally possible to ferment, or co-formulate, native hemp (that is, not previously extracted) with bacterial or fungal ingredients to achieve similar formulational benefits. In other words, the present invention also embraces bacterial- or fungal-fermented hemp, as well as hemp pomace. One skilled in the art is well able to adjust the dosing parameters discussed above to accommodate the higher constituent amounts, such as CBD, in the native hemp versus the hemp pomace.

As disclosed above, hemp pomace contains total dietary fiber (TDF) having a ratio of 1 part SDF to 30 parts IDF. As compared to higher SDF-containing botanicals, such as for example oat bran or bananas, a ratio of 1:30 SDF/IDF is a notably low SDF/IDF ratio and, for the purposes of the present invention, this high inclusion of IDF is extremely beneficial to delivery of CBD and other cannabinoids from an oral dosage form. SDF, upon oral administration, tends to create a sol/gel in the gastrointestinal tract, which in turns tends to retain in solution, i.e. binding or suspension, other molecules in its vicinity such as, in this case, cannabinoids. In other contexts, SDF is a highly desirable nutrient, that can even be partially digested by bacteria in the gut, but in the context of a cannabinoid delivery system SDF actually creates a binding system and subsequent removal from the body for an active agent, rather than a true delivery (release) system into the blood stream. By contrast, the high IDF inclusion assures the desirable release of the active agent promptly if not instantly in the stomach or upper gastrointestinal tract. Given this understanding of how the present oral dosage form works, moreover, it may be seen that the present oral composition, although botanical in initial source, is a highly engineered composition and not merely a product of nature at all. With the present oral dosage forms, the cannabinoid content is reduced (compared to native hemp) and yet the SDF/IDF ratio of 1:30, typical of native hemp, enhances delivery due to its high soluble fiber fraction. In fact, the engineering of the hemp into pomace creates a fascinating paradigm—when one realizes both that extraction is NOT always the desired processing and delivery method for hemp and that native hemp may be too high in THC content to be optimally useful as an oral dosage form, hemp pomace becomes a primary, premium product, and in no way a by-product of something else. (Even more interesting, in a world full of controlled-release and sustained-release pharmaceuticals, is the effective "flip" of the controlled release paradigm in the present invention, in that with the present invention the active agent delivery is designed to be instantaneous or at least prompt (not controlled or sustained), but the dosing per unit is deliberately reduced from its native form, rather than concentrated.) With the above understanding, therefore, the following terms are all synonymous: spent hemp pomace; hemp pomace, extracted pomace; extracted biomass; extracted hemp biomass; extracted hemp marc, extracted marc, native marc and native pomace. Moreover, inasmuch as the pomace is the supportable star of hemp extraction, in contrast to an extract, it is appropriate to call the present pomace "Hemp Extract" or "Whole Food Cannabinoid Extract," in the sense that it is the pomace that has been importantly wrested from the native hemp, not the relatively less useful traditional cannabinoid extraction products.

Important cannabinoids in hemp pomace are not limited to cannabidiol (CBD). Known significant cannabinoids other than THC include, without limitation, cannabigerol (CBG), cannabidivarin (CBDV), cannabichromene (CBC), cannabinol (CBN) and combinations thereof. Various strains of hemp tend to present different ratios of these cannabinoids and, in due course, the desired ratios will also inevitably be genetically engineered if not traditionally cross-bred. The ability of hemp pomace to serve as a uniquely effective delivery system for any and all cannabinoids and additional beneficial hemp components, typically in reduced amounts compared to their native hemp percentages, will apply to any hemp strain known or developed in the future.

Example 1

A quantity of native hemp is subjected to a traditional extraction of cannabinoids by moderate crushing and extraction of cannabinoids to create a "hemp pomace" which continued to include cannabinoids therein. The extraction may be by ethanol solvent extraction, carbon dioxide solvent extraction, vapor distillation, or flash pasteurization. At this writing, such extraction techniques for hemp (*Cannabis*) are known by those skilled in the art. The resulting pomace is carefully air dried at temperatures lower than 115 degrees Fahrenheit to prevent denaturing of all compounds and compositions in the pomace. A representative dried pomace prepared according to the above method steps contained 6% moisture and certain exemplary specifications listed in the below table. The dried pomace was divided and manufactured into compressed tablets to contain 1 gram by weight.

| QD252 - Protein - Combustion | Reference | Accreditation | Analysis Completed |
|---|---|---|---|
| | AOAC 990.03; AOAC 992.15 | A2LA ISO/IEC 17025:2005 | Jan. 15, 2020 |
| Parameter | | Result | |
| Protein | | 26.50% | |
| Nitrogen - Combustion | | 4.24% | |
| Protein Factor | | 6.25 | |

| QD250 -Ash | Reference | Accreditation | Analysis Completed |
|---|---|---|---|
| | AOAC 942.05 | A2LA ISO/IEC 17025:2005 | Jan. 15, 2020 |

| Parameter | Result |
|---|---|
| Ash | 17.74% |

| QD226 - Calories, Calculated | Reference | Accreditation | Analysis Completed |
|---|---|---|---|
| | CFR - Atwater calculation | A2LA ISO/IEC 17025:2005 | Jan. 17, 2020 |

| Parameter | Result |
|---|---|
| Calories Calculated | 323 kcal/100 g |

| QD038 - Carbohydrates, | Reference | Accreditation | Analysis Completed |
|---|---|---|---|
| | CFR 21-calc. | A2LA ISO/IEC 17025:2005 | Jan. 17, 2020 |

| Parameter | Result |
|---|---|
| Carbohydrates, Calculated | 46.25% |

| QD148 - Moisture by Vacuum | Reference | Accreditation | Analysis Completed |
|---|---|---|---|
| | AOAC 925.09 | A2LA ISO/IEC 17025:2005 | Jan. 17, 2020 |

| Parameter | Result |
|---|---|
| Moisture and Volatiles - Vacuum Oven | 6.0% |

| QD251 - Calcium by ICP | Reference | Accreditation | Analysis Completed |
|---|---|---|---|
| | AOAC 984.27 mod, 927.02 mod | A2LA ISO/IEC 17025:2005 | Jan. 15, 2020 |

Although the technology has been described with particularity above, with reference to specific materials and methods, the invention is only to be limited as is set forth in the following claims.

I claim:

1. A cannabinoid oral dosage form in unit dosage form, consisting essentially of hemp pomace, compounded as a tablet or within a capsule, powder or other unit dosage form as the predominant or exclusive ingredient, wherein said hemp pomace is the resulting material remaining after extraction and removal of cannabinoids therefrom, and having a soluble dietary fiber to insoluble dietary fiber ratio of 1:30 and a maximum cannabinoid dose per unit dosage form of 25 mg.

2. A cannabinoid oral dosage form in unit dosage form, consisting essentially of hemp pomace, compounded as a tablet or within a capsule, powder or other unit dosage form as the predominant or exclusive ingredient, wherein said hemp pomace is the resulting material remaining after extraction and removal of cannabinoids therefrom, and having a ratio of non hallucinogenic/addictive cannabinoid (CBD or CBG) to THC of 30:1-120:1.

3. The oral dosage form of claim 1, wherein each oral dosage form contains less than 10% water as moisture and wherein said cannabinoid is one or more of cannabidiol, cannabigerol, cannabidivarin, cannabichromene, or cannabinol.

4. The oral dosage form of claim 1, wherein said hemp pomace is fermented with a bacteria or fungus prior to compounding.

5. The oral dosage form of claim 1, wherein said dosage form contains no more than 10 mg cannabinoid per unit dosage form.

* * * * *